(12) United States Patent
Cremer

(10) Patent No.: US 6,238,698 B1
(45) Date of Patent: May 29, 2001

(54) ORAL PREPARATION CONTAINING AT LEAST ONE ACTIVE PHARMACEUTICAL SUBSTANCE IN A MATRIX CAPABLE OF SWELLING IN AN AQUEOUS MEDIUM

(75) Inventor: Karsten Cremer, Bonn (DE)

(73) Assignee: LTS Lohmann Therapie-Systeme GmbH, Neuwied (DE)

( * ) Notice: Subject to any disclaimer, the term of this patent is extended or adjusted under 35 U.S.C. 154(b) by 0 days.

(21) Appl. No.: 09/147,974

(22) PCT Filed: Aug. 29, 1997

(86) PCT No.: PCT/EP97/04717

§ 371 Date: Jul. 27, 1999

§ 102(e) Date: Jul. 27, 1999

(87) PCT Pub. No.: WO98/13028

PCT Pub. Date: Apr. 2, 1998

(30) Foreign Application Priority Data

Sep. 28, 1996 (DE) ............................................... 196 40 062

(51) Int. Cl.⁷ ................................ A61K 9/24; A61K 9/26; A61K 9/28
(52) U.S. Cl. ........................ 424/472; 424/468; 424/469; 424/474
(58) Field of Search ................................ 424/468, 469, 424/470, 488, 472, 474, 479, 482, 484

(56) References Cited

U.S. PATENT DOCUMENTS 5,422,123 6/1995 Conte et al. ........................ 424/479
5,603,956 * 2/1997 Mateescu et al. ................... 424/488

FOREIGN PATENT DOCUMENTS

| 43 41 442 C2 | 12/1993 | (DE) . |
| 44 16 926 A1 | 5/1994 | (DE) . |
| 94 02121 | 2/1994 | (WO) . |
| 94 21236 | 9/1994 | (WO) . |
| 0795 324 A2 | 9/1997 | (WO) . |

OTHER PUBLICATIONS

Lenaerts, et al., "Controlled Release of Theophylline from cross–linked amylose tablets", *Journ. Of Controlled Release* 1991 15; 39–46.

Sucker, Fuchs and Speiser, *Pharm. Techn.* 2, Auflage Jan. 1991.

\* cited by examiner

Primary Examiner—James M. Spear
(74) Attorney, Agent, or Firm—Jordan and Hamburg LLP

(57) ABSTRACT

An oral preparation, comprising at least one pharmaceutical active compound in a matrix which is swellable in aqueous medium, which is released from the matrix into the aqueous medium in a delayed manner on swelling thereof, while the matrix is largely resistant to disintegration during the release process, it is characterized in that it is a layered tablet with layers adhering to one another, of which at least one layer is the swellable matrix layer and at least another layer is an auxiliary and/or excipient layer, and in that the swellable matrix layer contains an amount of crosslinked amylose.

6 Claims, No Drawings

ORAL PREPARATION CONTAINING AT LEAST ONE ACTIVE PHARMACEUTICAL SUBSTANCE IN A MATRIX CAPABLE OF SWELLING IN AN AQUEOUS MEDIUM

This application is a 371 of PCT/EP97/04717 filed Aug. 29, 1997.

The invention relates to an oral preparation, comprising at least one pharmaceutical active compound in a matrix which is swellable in aqueous medium, which is released from the matrix into the aqueous medium in a delayed manner, while the matrix remains largely resistant to disintegration.

The delayed release of active compound from oral administration forms serves to avoid undesired plasma level variations. The construction variants with which delayed active compound release can be achieved also include layered tablets, in particular those in which the surface of the active compound-containing layer enlarges in the course of the release, whereby the release rate can be controlled in such a way that it remains largely constant. Depending on the design and the formulation of the layered tablet, this surface layer enlargement can result from the continuous erosion of one or more adjacent layers or from the swelling of the active compound-containing layer. The first-mentioned principle was described in the documents P 43 41 442.7 and P 44 16 926.4, the second, for example, in U.S. Pat. No. 5,422,123.

In the study of commercially available layered tablets having a swellable matrix layer, it was recognized as essential that a satisfactory surface enlargement due to swelling can only be achieved if mechanical stress on the tablet is largely avoided. If, to be precise, swelling takes place on entry of aqueous medium, a semi-solid gel of comparatively low mechanical stability results with increase in volume. Even the carrying-out of the disintegration test according to GP 10 using applied Plexiglass discs leads to a serious loss of shape of the swollen tablets.

The cause of the lack of mechanical stability of such matrix layers in the swollen state is the use of swellable polymers producing a swelling. They are mainly strongly hydrophilic polymers which, however, are insoluble or slowly soluble due to crosslinking, due to formation of crystalline fields or due to their large chain length. Examples of these types of polymers are croscarmellose, polyvinyl alcohol with a high degree of hydrolysis and high molecular weight hydroxypropylmethylcellulose. These very highly swellable polymers are also employed as disintegration accelerators or disintegrant in tablet formulations on account of this property (Sucker et. al., Pharmazeutische Technologie, Thieme Verlag, 1991, pp 174 et seq.). The preparation of swellable matrices which simultaneously remain mechanically stable when adequately swollen in aqueous medium is extremely problematical using the polymers mentioned, since their swelling-promoting properties cannot be separated from disintegration-promoting properties.

The object of the present invention is therefore to create an oral preparation having a matrix which is swellable on entry of aqueous medium, from which active compound is released into the aqueous medium in a delayed manner, and which is mechanically stable and resistant to disintegration in the swollen state up to the extensive end of the release.

The object is achieved according to the invention by providing a layered tablet with layers adhering to one another, of which at least one layer in the swellable matrix layer and at least another layer is an auxiliary or excipient layer, the swellable matrix layer containing cross linked amylase.

Crosslinked amylose swells in water, but differs from the customary swellable polymers by a surprisingly high mechanical strength in the swollen state. In this way, it is for the first time possible to create markedly improved, disintegration-resistant layered tablets in which the surface enlargement of the swelling matrix layer is also still effective if mechanical stresses occur, such as, for example, in the disintegration test or after administration in the gastrointestinal tract.

Amylose is a constituent of natural starches, which is contained mainly in the interior of starch grains with a content of approximately 15 to 30%, and consists of unbranched chains with D-glucopyranose units which are linked with one another α-1,4-glycosidically. By reaction with agents such as, for example, epichlorohydrin or 2,3-dibromopropanol, amylose can be effectively crosslinked, for which purpose a proportion of 0.1 to 10% of crosslinker, based on the amylose, is necessary.

It is disclosed in U.S. Pat. No. 5,456,921 that crosslinked amylose, in particular that with a relatively low degree of crosslinking, is distinguished in particular by a strong tendency to form hydrogen bridges between the molecular chains, which in turn leads to large cohesive forces which can maintain the mechanical stability of a preparation or of a tablet even in the swollen state. In this patent specification, various homogeneous, i.e. single-layered tablets with crosslinked amylose, are also described which release their active compound, e.g. theophylline, in a uniformly delayed manner. Different types of mechanisms for the control of the release rate are discussed here, the favoured type being based on control of the kinetics of the entry of water by intermolecular hydrogen bridges and this being attributed the greatest importance for the release rate.

Surprisingly, it has now been achieved by the invention for the first time that layered tablets having at least one swellable matrix layer, whose release kinetics are controlled by means of the surface growth of the matrix layer due to swelling, with a content of amylose have a distinctly increased measure of mechanical strength compared with the prior art, whereby reliable control of the release kinetics is guaranteed even on mechanical stress of the tablet, because their surface growth takes place despite this stress without them disintegrating during release.

The term layered tablet in the sense of this invention relates to a tablet made of at least two layers in each case -adhering to one another and prepared by compressing powder or granules. A layered tablet can additionally have further features, such as, for example, a coating of a sugar-containing or polymer-containing composition or a coating produced by compressing powder or granules. In these cases, the layered tablet would also be described as a sugarcoated tablet, film-coated tablet or press-coated tablet.

The layered tablet of the invention has an active compound-containing matrix layer, this term being understood as a major term for all layer compositions in which active compound is uniformly dispersed or embedded. A layered tablet according to the invention can also contain more than one active compound-containing matrix layer, for example if more than one active compound is intended to be released in delayed form, or various active compound components are intended to be released from different layers at a different rate.

Accordingly, a layered tablet according to the invention can contain one or more active compounds.

The active compound-containing matrix layer is swellable on entry of aqueous medium, i.e. in contact with water, physiological or artificial gastric or intestinal juice the matrix layer takes up water and constituents optionally dissolved in water with an increase in volume, a large part of the swelling water typically being intercalated between polymer chains which are contained in a matrix preparation.

In the sense of the invention, an extensive resistance to disintegration of a matrix layer during the release process means that the disintegration is not complete in the disintegration test according to GP 10 as long as at least the greater part of the active compound dose contained in the matrix layer has been released. A delayed release of active compound as a rule takes place over at least several hours, all types of release profiles, i.e. linear and non-linear, but also complex profiles with an initial and a maintenance dose etc., being included.

The layered tablet of the invention according to the main claim is different from known layered tablets of the prior art in that it has a swellable matrix layer with a content of crosslinked amyloses. Preferred contents of crosslinked amylose in the matrix layer are between 30 and 99.5%. While very low-dose active compounds allow a high content of crosslinked amylose, larger active compound doses with respect to a maximum administrable tablet size require a more or less marked reduction in the auxiliary content. In order to be able to allow the positive effects of the crosslinked amylose described above to come to bear, however, as a rule a content of at least 20% will have to be employed. Even lower use amounts are admittedly less preferred, but likewise conform to the invention, since they can likewise lead through the choice of special pharmaceutical technological additive measures such as, for example, the use of special particle forms and particle size distributions, particularly press conditions, agglomeration processes, etc., to a layered tablet according to the invention.

The main advantage of a preparation according to the invention is accordingly to be been in that a layered tablet prepared with it regardless of mechanical tumbling stress proves its cohesive strength in the gastrointestinal tract and thus maintains a uniformly delayed release of its active compound content up to its exhaustion.

What is claimed is:

1. A layered tablet for oral administration of a pharmaceutically active compound, the layered tablet comprising a matrix layer and an auxiliary or excipient layer adhered to each other wherein the matrix layer comprises a pharmaceutically active compound and cross linked amylose so that the matrix layer swells in an aqueous medium resulting in release of the pharmaceutically active compound in a delayed manner upon said swelling and wherein the matrix layer and the auxiliary or excipient layer are resistant to disintegration during this release process and the auxiliary or excipient layer increases the resistance of the matrix layer to disintegration during said release process to prevent disintegration of the matrix layer at least until release of the pharmaceutically active compound is essentially completed the rate of release of the pharmaceutically active compound being controlled by surface growth of the matrix layer resulting from said swelling and said prevention of disintegration preventing uncontrolled increases in the surface area of the matrix which would result from disintegration of the matrix layer.

2. The layered tablet of claim 1 wherein the amount of cross linked amylose in the matrix layer is between 20 and 99.5% by weight.

3. The layered tablet of claim 1 wherein the release rate over the greater part of the release period is largely constant.

4. The layered tablet of claim 1 wherein it contains more than one active compound.

5. The layered tablet of claim 1 which is formed as a core of a film-coated or press-coated tablet.

6. The layered tablet of claim 1 wherein the delayed manner in which the pharmaceutically active compound is released from the matrix layer into the aqueous medium is linear, non-linear or complex.

* * * * *